US007011839B2

(12) United States Patent
Ciszewski

(10) Patent No.: US 7,011,839 B2
(45) Date of Patent: Mar. 14, 2006

(54) OTIC MICROBIAL COMBINATION FOR TREATMENT OF ANIMALS WITH RUPTURED TYMPANIC MEMBRANE

(75) Inventor: Daniel Ciszewski, Tonganoxie, KS (US)

(73) Assignee: Baya Corporation, Pittsburgh, PA (US)

( * ) Notice: Subject to any disclaimer, the term of this patent is extended or adjusted under 35 U.S.C. 154(b) by 0 days.

(21) Appl. No.: 10/309,918

(22) Filed: Dec. 4, 2002

(65) Prior Publication Data

US 2003/0119804 A1    Jun. 26, 2003

Related U.S. Application Data

(63) Continuation of application No. 09/669,514, filed on Sep. 25, 2000, now abandoned.

(51) Int. Cl.
*A01N 25/32* (2006.01)
(52) U.S. Cl. .................. 424/406; 424/450; 514/186; 514/252.17
(58) Field of Classification Search ............... 424/405, 424/406; 574/186, 252.17
See application file for complete search history.

(56) References Cited

U.S. PATENT DOCUMENTS

| 3,761,590 A | 9/1973 | Fox, Jr. ..................... 424/228 |
| 4,404,197 A | 9/1983 | Fox, Jr. et al. ............. 424/229 |
| 5,753,269 A | 5/1998 | Groh et al. ................. 424/618 |

FOREIGN PATENT DOCUMENTS

| EP | 0337328 | 10/1989 |
| WO | 9639146 | 12/1996 |

OTHER PUBLICATIONS

Kohonen, et al. Penetration of Trimethoprim Sulfadiazine into Middle Ear Fluid in Secretory Otitis Media, Int. J. Pediatr. Otorhinolaryngol. 6:89-94, 1983 (journal abstract).
The Compendium, Small Animal, vol. 12, No. 3, Mar. 1990, Continuing Education Article #2, pp. 331-337, P. D. Mansfield, "Ototoxicity in Dogs and Cats".
Toxicology Letters, 52, month unavailable, 1990, pp. 227-251, P. J. Govaerts et al, Aminoglycoside-Induced Ototoxicity.
Ann Otol Thinol Laryngol, 95, month unavailable, 1986, pp. 404-408, T. Harada et al, "Ototoxicity of Neomycin And Its Penetration Through The Round Window Membrane Into The Perilymph".
Acta olo-laryny-ologica, 68, month unavailable, 1969, pp. 90-97, A. Kohonen et al, "Cochlear Damage From Ototoxic Antibiotics By Intratympanic Application".
Ann Otol Rhinol Laryngol, 99, month unavailable, 1990, pp. 42-45, T. Morizono, "Toxicity of Ototopical Drugs: Animal Modeling".
J. Pharm. Pharmac., 30, month unavailable, 1978, pp. 236-239, F. L. Parker et al, "The Effect of Various Topical Antibiotic and Anti-bacterial Agents on the Middle and Inner Ear of the Guinea-Pig".
Acta Ololaryngol (Stockh), 97, month unavailable, 1984, pp. 593-610, S. Saijo et al, "Distribution of HRP in the Inner Ear after Injection into the Middle Ear Cavity".
Arch Otolaryngol Head Neck Surg, vol. 113, Jun. 1987, pp. 625-629, P. A. Schachern et al, "The Permeability of the Round Window Membrane During Otitis Media".
Am J. Vet Res, vol. 56, No. 4, Apr. 1995, pp. 532-538, G. M. Strain, "Ototoxicity Assessment of a Gentamicin Sulfate Otic Preparation in Dogs".
Am. J. Otolaryngol, 9, month unavailable, 1988, pp. 327-335, O. Spandow et al, "The Round Window as Access Route for Agents Injurious to the Inner Ear".
Audiology 12, month unavailable, 1973, pp. 350-363, H. Stupp et al, "Inner Ear Concentrations and Ototoxicity of Different Antibiotics in Local and Systemic Application".
Am J Otolaryngol, May 5, 1984, pp. 166-176, C. G. Wright et al, "ototoxicity of Otic Drops Applied to the Middle Ear in the Chincilla".

*Primary Examiner*—Neil S. Levy

(57) ABSTRACT

Disclosed herein is an improved composition that is useful in treating otic infections comprising an antimicrobial and silver sulfadiazine in a therapeutically effective combination to treat otic infections in animals, the improvement comprising the composition which can be used safely to treat animals with a ruptured tympanic membrane.

15 Claims, No Drawings

OTIC MICROBIAL COMBINATION FOR TREATMENT OF ANIMALS WITH RUPTURED TYMPANIC MEMBRANE

This application is a continuing application of U.S. Ser. No. 09/669,514, filed Sep. 25, 2000, now abandoned.

BACKGROUND OF THE INVENTION

1. Field of Invention

The present invention relates to otic formulations and antimicrobial agents and more specifically to otic formulations containing a combination of antimicrobials such as quinolones and silver sulfadiazine. More specifically, the invention relates to treatment of animals with ruptured tympanic membrane.

2. Brief Description of the Prior Art

U.S. Pat. No. 4,404,197 discloses the use of certain quinolones and silver sulfadiazine in treating burns. More specifically, the patent discloses compositions that include silver sulfadiazine and 1-ethyl-6-fluoro-1,4-dihydro-4-oxo-7-(1-piperazinyl)-3-quinolone carboxylic acid or its metal salts, e.g., silver, zinc, cobalt or cerium salts. Distinctly, the patent teaches the use of these compositions in treating burns, and in combating topical, surface or skin infections, including microbial and fungal infections and the like. However, the patent fails to teach or suggest the use of the compositions for otic applications.

U.S. Pat. No. 3,761,590 discloses the use of silver sulfadiazine alone in burn therapy. Silver sulfadiazine, preferably in a water-dispersible hydrophilic carrier, is applied to the burn.

Bogaard et al, Dep. Med. Microbiol., Univ. Limburg, Netherlands discloses the use of silver sulfadiazine cream in treating chronic *Pseudomonas* infection of the external auditory canal in dogs.

U.S. Pat. No. 5,753,269 discloses an otic composition that is useful in treating otic infections comprising an antimicrobial such as a quinolone or a salt thereof and silver sulfadiazine in a therapeutically effective combination to treat otic infections in animals. It has surprisingly been found that this composition is safe and effective in treating otic infection even in instances of ruptured tympanic membrane. Heretofore, art-known treatments of animals with a ruptured tympanic membrane produced adverse effects such as loss of hearing. It is believed that most antimicrobial compounds (e.g. aminoglycosides) have a toxic effect on the hair cells in the cochlea. Such toxicity manifests in eventual loss of hearing. It is worth noting that these compounds may not have toxicity when applied topically on the skin or into the external ear canal where the tympanic membrane is intact, since this membrane acts as a barrier to direct entry of the antimicrobial into the inner ear. However, in instances where the tympanic membrane is ruptured there is loss of the protective barrier and the rupture may provides a ready access of the compounds to the cochlea, increasing the probability for toxicity.

SUMMARY OF THE INVENTION

In contrast, the present invention provides an improved composition that is useful in treating otic infections comprising an antimicrobial and silver sulfadiazine in a therapeutically effective combination to treat otic infections in animals, the improvement comprising the composition which can be used safely to treat animals with a ruptured tympanic membrane. The invention further encompasses an improved method of treating an otic infection in an animal comprising administering a composition an antimicrobial and silver sulfadiazine in a therapeutically effective combination to treat the otic infection, the improvement comprising administering the composition to an animal with a ruptured tympanic membrane.

The composition containing a combination of an antimicrobial such as an antibacterial agent which is preferably a quinolone and silver sulfadiazine can be administered as such or with a physiologically acceptable carrier such as an oil-in-water emulsion. The composition can be used to safely and efficaciously treat otic infections caused by the bacteria *Pseudomonas,* or fungus, *Malessezia pachydermitis*. The invention is described more fully hereunder.

DETAILED DESCRIPTION OF THE INVENTION

As set forth above, the present invention relates to a composition that is useful in treating otic infections of animals with a ruptured tympanic membrane. The composition comprises a therapeutically effective combination of an antimicrobial such an antibacterial agent which is preferably a quinolone or a salt thereof and silver sulfadiazine. Typically, the quinolone is a fluorinated quinolone. The effective combination is described hereunder with specificity as to quinolones. The invention, however, encompasses combinations of silver sulfadiazine and other antimicrobial which can combined with the silver sulfadiazine to provide effective treatment of otic infections in the manner of the combination of silver sulfadiazine and quinolones.

Non-limiting examples of the fluorinated quinolone can be selected from the group consisting of Enrofloxacin; 6-Fluoro-1,4-dihydrodihydro-1-(methylamino)-7-(4-methyl-1-piperazinyl)-4-oxo-3-quinolonecarboxylic acid (Amifloxacin); Benofloxacin; 6-Fluoro-1-(4-fluorophenyl)-1,4-dihydro-7-(4-methyl-1-piperazinyl)-4-oxo-3-quinolonecarboxylic acid (Difloxacin); Flerofloxacin; 6,8-Difluoro-1-(2-fluoroethyl))-1,4-dihydro-7-(4-methyl-1-piperazinyl)-4-oxo-3-quinolonecarboxylic acid (Fleroxacin); 1-Ethyl-6,8-difluoro-1,4-dihydro-7-(3-methyl-1-piperazinyl)-4-oxo-3-quinolonecarboxylic acid (Lomefloxacin); Marbofloxacin; 1-ethyl-6-fluoro-1,4-dihydro-4-oxo-7-(piperazinyl)-3-quinolonecarboxylic acid (Norfloxacin); 9-Fluoro-2,3-dihydro-3-methyl-10-(4-methyl-1-piperazinyl)-7-oxo-7H-pyrido[1,2,3-de]-1,4-benzoxazine-6-carboxylic acid (Ofloxacin); Perfloxacin; Rufloxacin; Sarafloxacin; and Temafloxacin. The fluorinated quinolone preferred herein is Enrofloxacin. U.S. Pat. No. 4,556,658 which is incorporated herein by reference provides an illustrative but non-limiting description of the quinolone with particularity to Enrofloxacin and a method of preparing the same.

The quinolone or the salt thereof and the silver sulfadiazine are employed in an amount sufficient to provide a composition that would be pharmaceutically effective. The quinolone or the salt thereof can be employed in an amount of 0.005 to 1.5 percent by weight of the composition and preferably 0.1 to 1 percent by weight of the composition. Silver sulfadiazine can be employed in an amount of 0.05 to 2 percent of the composition, and preferably in an amount of 0.5 to 1.5 percent of the composition.

In the preparation of the composition, the quinolone and silver sulfadiazine can be combined in any convenient manner. For example, comminuted silver sulfadiazine and the quinolone can be mixed with each other. The composition can be used directly or preferably in formulation with a pharmaceutically acceptable physiological carrier.

A non-limiting example of a pharmaceutically acceptable physiological carrier can be an oil in water emulsion. Typically, the oil is a non-irritating emollient oil. An illustrative but non-limiting example thereof can be selected from the group consisting of a mineral oil, vegetable oil and a reformed vegetable oil of known composition. More specific but non-limiting examples of the oil can be selected from the group consisting of peanut oil, sesame seed oil, cottonseed oil, etc.; a medium chain ($C_6$ to $C_{12}$) triglycerides (e.g., Miglyol Neutral Oils 810, 812, 818, 829, 840, etc.) available from Huls America Inc. Typical emulsifiers employed herein can be selected from the group consisting of Span 60 which is sorbitan monostearate and Tween 60, which is Polysorbate 60 (both of which are available from ICI Americas). Preferably, the emulsifiers are nonionic. The emulsifiers can be employed in an amount of 1.5 to 6.5 percent by weight of the composition and preferably 3.0 to 5.0 percent by weight of the composition. The hydrophobic phase of the emulsion can be in an amount of 15.0 to 25.0 percent by weight of the composition and preferably 18.0 to 22.0 percent by weight of the composition.

It is a distinct feature of the invention that the composition of the invention can be formulated as an emulsion base comprising oil in water emulsions described herein. Heretofore, silver sulfadiazine had been formulated as a cream base or a solid synthetic dressing for use in burn therapy. Related silver nitrate solutions were considered undesirable.

In addition to the above components, a formulation of the composition of the invention may contain other components such as preservatives (benzyl alcohol, parabens, or benzoates), stabilizers (cetyl stearyl alcohol, glycerol esters), odor masking agents, and coloring agents.

The following is an illustrative but non-limiting description of a method of providing the compositions of the invention. In a properly equipped vessel, an emulsifier and a fatty acid alcohol are heated in an oil to form a suspension, and the active ingredients are added to the suspension. In a different vessel, an emulsifier is added to hot water to form an aqueous solution. To the solution are added a preservative and the suspension with vigorous mixing. The resulting mixture comprising the composition of this invention is effective in treating otic infections.

In treating an otic infection, the composition is preferably administered by applying it otically in a pharmaceutically effective amount. The composition can be applied at a dose of five to twenty drops per ear and preferably at a dose of eight to twelve drops per ear as needed to coat the ear canal. The composition can be applied as often as necessary, preferably twice a day.

This and other aspects of the invention are further illustrated by the following non-limiting examples in which all parts and percentages are by weight unless otherwise specified.

EXAMPLES

The following examples illustrate the otic compositions of the present invention and methods of preparing and using the same. In the present embodiment of the invention, the silver sulfadiazine and the quinolone are combined as follows.

Polysorbate 60 (Tween 60) was added to water in a stainless steel jacketed tank at a temperature of 50 to 60° C. The resulting aqueous solution was heated to 61 to 75° C. At a temperature of 66° C., a preservative (benzyl alcohol) was added to the aqueous solution while mixing three to ten minutes.

At a temperature of 75° C. Enrofloxacin and silver sulfadiazine were added to Mygliol Oil in a separate vessel over a period of three to five minutes. Sorbitan Monostearate (Span 60) and cetyl stearyl alcohol were added to the oil mixture. The resulting oil mixture was heated to 62 to 75° C. The oil mixture was then added with vigorous mixing to the aqueous solution at a temperature of 66° C. over a period of three to five minutes. The resulting composition was cooled to 35 to 45° C. and homogenized by mixing with a high shear emulsifier or running through a homogenizer. The composition was further cooled to 25 to 30° C. The final composition was packaged in appropriate containers.

Examples 1–3 describe the use of the above method and the following ingredients in the parts by weight listed below to prepare formulations containing the compositions of the invention.

Example 1

| Ingredients | Parts By Weight |
| --- | --- |
| Enrofloxacin | 0.005–1.5 |
| Silver sulfadiazine(SSD) | 0.05–2.0 |
| Polysorbate 60 | 0.5–3.5 |
| Sorbitan monostearate | 0.5–3.0 |
| Cetyl stearyl alcohol | 0.5–3.0 |
| Benzyl alcohol | 1.0–3.0 |
| Miglyol Oil | 8–18 |
| Water | 89.4–68 |

Example 2

| Ingredients | Parts By Weight |
| --- | --- |
| Enrofloxacin | 0.5–1.0 |
| Silver sulfadiazine(SSD) | 0.5–1.5 |
| Polysorbate 60 | 1.0–3.0 |
| Sorbitan monostearate | 1.0–2.0 |
| Cetyl stearyl alcohol | 1.0–2.0 |
| Benzyl alcohol | 1.5–2.5 |
| Miglyol Oil | 12–16 |
| Water | 85–74 |

Example 3

| Ingredients | Parts By Weight |
| --- | --- |
| Enrofloxacin | 0.5 |
| Silver sulfadiazine(SSD) | 1.0 |
| Polysorbate 60 | 2.5 |
| Sorbitan monostearate | 1.5 |
| Cetyl stearyl alcohol | 1.5 |
| Benzyl alcohol | 2.0 |
| Miglyol Oil | 14.5 |
| Water | 76.5 |

Example 4

An in vitro microbiology study of the combination of the Enrofloxacin (quinolone) and sulfadiazine was conducted on multiple canine otic pathogens. The study was conducted under the National Committee for Clinical Laboratory Standards (NCCLS) guidelines employing ATCC control organisms for each agar plate tested. Initially, minimum inhibitory concentrations (MICs) were established for each active ingredient. Both enrofloxacin and silver sulfadiazine (SSD) were active on common dermal (otic) pathogens, based on MICs. Each has a different mode of action, though both are bactericidal. The different modes of action reduce the potential for-resistance development. Additionally, Enrofloxacin was not effective on *Malassezia* or *Candida* at the concentrations tested. Silver sulfadiazine was effective on both. Evidence of *Malassezia* activity by silver sulfadiazine has not been reported previously.

Using MIC data, there were prepared agar plates containing serial dilutions of each antimicrobial in combination, using a standard checkerboard system. To identify possible interactions between the Enrofloxacin and the silver sulfadiazine, dilutions were prepared, that were for the most part, from three dilutions above to three dilutions below the MIC for each of the antimicrobials. The patterns of growth (inhibition) of the individual isolates, following exposure to the antimicrobials, were compared. Those of a single genera with the same response were grouped together. All isolates were then subjected to a mathematical calculation designed to indicate whether the antimicrobials were antagonistic, synergistic, or somewhere between. The standard calculation called a Fractional Inhibitory Concentration (FIC) Index is presented below $$\frac{X}{MIC_x} + \frac{Y}{MIC_y} = FIC_x + FIC_y = FIC \text{ index}$$

wherein X is equal to a concentration of drug X which is the lowest inhibitory concentration in its row of the checkerboard, and Y is equal to a concentration in its row of the checkerboard.

FIC index equal to or less than 0.5 indicates synergism.

FIC index equal to or greater than 2.0 indicates antagonism.

FIC index equal to or greater than 0.5 but less than 2.0 indicates no effect.

For the purpose of comparison, the Enrofloxacin was also combined with clotrimazole. Clotrimazole has antifungal activity but essentially no activity on bacteria. The same series of pathogens were used to evaluate both antimicrobial combinations. FIC data from the study indicating response observed for the two combinations are presented below. (Table 1).

TABLE 1

Antimicrobial Range of Interaction

| Organism | Fractional Inhibitory Concentration Index | |
|---|---|---|
| | Enro* + SSD | Enro + Clotr |
| *Pseudomonas aeruginosa* (15)** | 0.507 to 0.75 | 1.167 to 2.67 |
| *Staphylococcus intermedius* (12) | 1.5 | 1.5 |
| *Escherichia coli* (7) | 0.36 to 1.5 | 0.8 to 1.8 |
| *Klebsiella pneumoniae* (5) | 0.62 to 1.5 | 1.8 to 2.3 |
| Beta-hemol *Streptococcus* (9) | 0.625 to 1.5 | 0.75 to 2.25 |

TABLE 1-continued

Antimicrobial Range of Interaction

| Organism | Fractional Inhibitory Concentration Index | |
|---|---|---|
| | Enro* + SSD | Enro + Clotr |
| *Malassezia* sp (12) | 1.5 | 0.56 to 1.5 |
| *Candida* sp (4) | 1.5 to 1.75 | 1.5 |

*Drug abbreviations are:
Enro = Enrofloxacin,
SSD = Silver Sulfadiazine
Clotr = Clotrimazole
**Numbers in parenthesis indicates numbers of isolates tested.

As to the isolates reported above, the combination of the Enrofloxacin and silver sulfadiazine had no values in the antagonistic category. The FIC indices for many of the bacterial isolates were less than 1.0 showing a clear tendency towards additive effect. A few calculations showed synergism. There was less of a tendency to an additive effect with *Malassezia* and *Candida*.

The additive effect of the Enrofloxacin and the silver sulfadiazine could not have been predicted because the combination of antimicrobials with different modes of activity could have just as easily demonstrated antagonism. Antagonism was clearly demonstrated, for example, with the combination of Enrofloxacin and Clotrimazole. In three of the five bacterial genera reported above, a score of greater than 2 was calculated. Clotrimazole does not have antibacterial activity, yet the data indicated that the drug apparently interfered with the antibacterial effect of the Enrofloxacin.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An improved method of treating an otic infection in an animal comprising administering a composition comprising an antimicrobial and silver sulfadiazine in a therapeutically effective combination to treat the otic infection, the improvement comprising administering the composition to an animal with a ruptured tympanic membrane.

2. The method of claim 1, wherein said composition is administered in a pharmaceutically effective amount.

3. The method of claim 1, wherein said composition is administered on a twice daily basis.

4. The method of claim 1, wherein said enrofloxacin is present in an amount from about 0.005 to about 1.5 percent by weight of the composition.

5. The method of claim 4, wherein said enrofloxacin is present in an amount from about 0.1 to about 1.0 percent by weight of the composition.

6. The method of claim 1, wherein said silver sulfadiazine is present in an amount from about 0.05 to about 2.0 percent by weight of the composition.

7. The method of claim 6, wherein said silver sulfadiazine is present in an amount from about 0.5 to about 1.5 percent by weight of the composition.

8. The method of claim 1, wherein said composition further comprises a physiologically acceptable carrier.

9. The method of claim 8, wherein said carrier comprises an emulsion.

10. The method of claim 9, wherein said emulsion comprises and oil in water emulsion.

11. The method of claim 10, wherein said oil is selected from the group consisting of mineral oil, vegetable oil and reformed vegetable oil.

12. The method of claim 11, wherein said oil is selected from the group consisting of peanut oil, sesame seed oil, cotton seed oil, and medium chain triglycerides.

13. The method of claim 9, wherein said emulsion comprises an emulsifier that is present in an amount of about 1.5 to about 6.5 percent by weight of the composition.

14. The method of claim 13, wherein said emulsifier is selected from the group consisting of sorbitan monostearate and polysorbate 60.

15. The method of claim 9, wherein said emulsion comprises a non-aqueous phase in an amount of about 15 to about 25 percent by weight of the composition.

* * * * *